United States Patent [19]

Schliebs et al.

[11] 4,102,949
[45] Jul. 25, 1978

[54] PRODUCTION OF 3,4-DIHYDROXY PHOSPHOLANE OXIDES

[75] Inventors: Reinhard Schliebs; Hans-Dieter Block, both of Cologne, Germany

[73] Assignee: Bayer Aktiengesellschaft, Leverkusen, Germany

[21] Appl. No.: 758,527

[22] Filed: Jan. 11, 1977

[30] Foreign Application Priority Data

Jan. 24, 1976 [DE] Fed. Rep. of Germany ....... 2602646

[51] Int. Cl.$^2$ ............................. C07F 9/32; C07F 9/53
[52] U.S. Cl. .................................. 260/985; 260/936; 260/606.5 P
[58] Field of Search .................. 260/985, 936, 606.5 P

[56] References Cited

U.S. PATENT DOCUMENTS 3,723,520  3/1973  Smith et al. ..................... 260/936

Primary Examiner—Anton H. Sutto
Attorney, Agent, or Firm—Burgess, Dinklage & Sprung

[57] ABSTRACT

A process for the preparation of a 3,4-dihydroxy phsopholane oxide of the formula

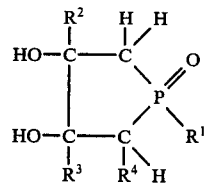

in which
  $R^1$ represents an alkyl, alkoxy, alkenyl, alkenyloxy, alkinyl or alkinyloxy with up to 18 carbon atoms and substitution products thereof; aryl and aryloxy having up to 14 carbon atoms and substitution products thereof; cycloalkyl and cycloalkoxy having up to 6 ring carbon atoms and substitution products thereof; dialkylamino having up to 6 carbon atoms per alkyl radical and substitution products thereof; and N-hetero-radicals, and
  $R^2$, $R^3$ and $R^4$ independently of one another represent a $C_1$-$C_4$-alkyl radical or hydrogen,
comprising reacting a phospholene oxide of the formula

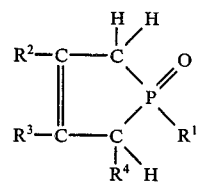

with hydrogen peroxide in the presence of a catalytic amount of an osmium compound at a temperature in the range of about 20° to 150° C, especially about 35° to 100° C.

2 Claims, No Drawings

PRODUCTION OF 3,4-DIHYDROXY PHOSPHOLANE OXIDES

This invention relates to a process for the production of 3,4-dihydroxy phospholane oxides by reacting phospholene oxide derivatives with hydrogen peroxide in the presence of osmium compounds as catalyst.

Phospholene oxides and phospholane oxides are known to be effective catalysts for the conversion of isocyanates into carbodiimides with the elimination of carbon dioxide. Various attempts have already been made to produce functional derivatives of these compounds in order thereby to obtain monomers, capable of incorporation into various classes of carbodiimide-forming polymers. However, it is only difunctional phospholene and phospholane oxides which can be used for incorporation, for example into polyesters and polycarbonates, because otherwise it would only be possible to obtain very short and hence soluble polymer chains.

3,4-Dihydroxy phospholane oxides are known representatives of difunctional phospholane oxides of this type (B. A. Arbusow et al., Bull. Acad. Sci. USSR 1969, IV, pages 2079 to 2082). These compounds are obtained from the corresponding 3,4-epoxy phospholane oxides by hydrolysis for 13 hours in boiling sulfuric acid solution. The 3,4-epoxy phospholane oxides are in turn obtained in a yield of from 35 to 55% from the 3-phospholene oxides and peracetic acid (B. A. Arbusow et al., Bull. Acad. Sci. USSR 1968, II, pages 1237 to 1242).

The disadvantage of this known process is that it is relatively complicated and only gives the required products in moderate yields. Accordingly, the object of the present invention is to provide an improved process for producing 3,4-dihydroxy phospholane oxides.

Accordingly, the present invention relates to a process for the production of 3,4-dihydroxy phospholane oxides corresponding to the general formula (I):

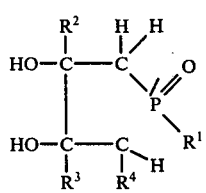

in which
$R^1$ represents an alkyl, alkoxy, alkenyl, alkenyloxy, alkinyl or alkinyloxy with up to 18 carbon atoms and substitution products thereof; aryl and aryloxy having up to 14 carbon atoms and substitution products thereof; cycloalkyl and cycloalkoxy having up to 6 ring carbon atoms and substitution products thereof; dialkylamino having up to 6 carbon atoms per alkyl radical and substitution products thereof; and N-hetero-radicals, and
$R^2$, $R^3$ and $R^4$ independently of one another represent a $C_1$–$C_4$-alkyl radical or hydrogen,
distinguished by the fact that phospholene oxide derivatives corresponding to the general formula (II):

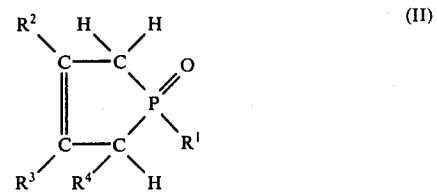

in which
$R^1$, $R^2$, $R^3$ and $R^4$ have the same meaning as in formula (I), are reacted with hydrogen peroxide in the presence of catalytic quantities of osmium compounds at temperatures in the range of about 20° to 150° C and preferably at temperatures in the range of about 35° to 100° C.

Preferred substituents for $R^1$ are alkyl or alkoxy of up to 6 carbon atoms, especially up to 4 carbon atoms; hydroxy, halo, lower alkoxy, carbo-lower alkoxy, phenyl, phenoxy, substituted-phenyl and substituted-phenoxy substitution products of any of the foregoing; alkenyl, alkinyl, alkenoxy or alkinoxy of up to 4 carbon atoms; cycloalkyl and cycloalkyloxy having up to 6 ring carbon atoms; dialkylamino and di-hydroxy-alkylamino with up to 4 carbon atoms per alkyl radical; phenyl; halophenyl; lower alkyl phenyl; morpholino; piperidino; imidazolyl; and oxazolidinyl.

The starting materials for the process according to the invention, phospholene oxide derivatives such as, for example, phosphine oxides, phosphinic acid esters or phosphinic acid amides (corresponding to formula II), are known and may be obtained by known methods (cf. G. M. Kosolapoff, L. Maier, Organic Phosphorus Compounds, Wiley-Interscience, New York, 1972, Vol. 3, pages 370 to 371, pages 458 to 463 and Vol. 4, pages 9 to 10, page 48). The following are examples of 5-membered unsaturated phosphine oxides such as these:
1-methyl-1-oxo-3-phospholene
1-ethyl-1-oxo-3-phospholene
1-butyl-1-oxo-3-phospholene
1-(2-ethylhexyl)-1-oxo-3-phospholene
1-(2-chloroethyl)-2-oxo-3-phospholene
1-phenyl-1-oxo-3-phospholene
1-p-tolyl-1-oxo-3-phospholene
1-chloromethyl-1-oxo-3-phospholene
1,3-dimethyl-1-oxo-3-phospholene
1,2-dimethyl-1-oxo-3-phospholene
1-chlorophenyl-1-oxo-3-phospholene
1,3,4-trimethyl-1-oxo-3-phospholene
1,2,4-trimethyl-1-oxo-3-phospholene
1,2,2-trimethyl-1-oxo-3-phospholene
1-phenyl-3-methyl-1-oxo-3-phospholene
1-phenyl-2,3-dimethyl-1-oxo-3-phospholene
and of phosphinic acid esters and amides such as these:
1-methoxy-1-oxo-3-phospholene
1-ethoxy-1-oxo-3-phospholene
1-n-propoxy-1-oxo-3-phospholene
1-i-propoxy-1-oxo-3-phospholene
1-n-butoxy-1-oxo-3-phospholene
1-sec.-butoxy-1-oxo-3-phospholene
1-i-butoxy-1-oxo-3-phospholene
1-tert.-butoxy-1-oxo-3-phospholene
1-pentyloxy-1-oxo-3-phospholene
1-cyclohexyloxy-1-oxo-3-phospholene
1-(2-ethylhexyloxy)-1-oxo-3-phospholene
1-dodecyloxy-1-oxo-3-phospholene
1-octadecyl-1-oxo-3-phospholene 1-benzyloxy-1-oxo-3-phospholene
1-phenoxyethoxy-1-oxo-3-phospholene
1-p-chlorophenoxyethoxy-1-oxo-3-phospholene
1-β-chloroethoxy-1-oxo-3-phospholene
1-β-hydroxyethoxy-1-oxo-3-phospholene
1-β-butyloxyethoxy-1-oxo-3-phospholene
1-β-hydroxypropoxy-1-oxo-3-phospholene
1-carbethoxymethoxy-1-oxo-3-phospholene
1-carbethoxyethoxy-1-oxo-3-phospholene
1-allyloxy-1-oxo-3-phospholene
1-propargyloxy-1-oxo-3-phospholene
1-dimethylamino-1-oxo-3-phospholene
1-diethylamino-1-oxo-3-phospholene
1-bis-2-hydroxyethylamino-1-oxo-3-phospholene
1-bis-2-hydroxypropylamino-1-oxo-3-phospholene
1-morpholino-1-oxo-3-phospholene
1-piperidino-1-oxo-3-phospholene
1-imidazolyl-1-oxo-3-phospholene
1-oxazolidinyl-1-oxo-3-phospholene and also the phosphinic acid esters and amides which can be derived from the phosphinic acid esters and amides as mentioned above by substitution with the substituents $R^2$, $R^3$ and $R^4$ of formula (II).

Instead of using the phospholene oxides of formula (II), it is also possible to use compounds which are converted into phospholene oxides under the reaction conditions. Compounds such as these include, for example, the phospholenes with trivalent phosphorus and the phospholene sulfides which are converted into phospholene oxides by oxidizing agents such as hydrogen peroxide. In these cases, it is necessary to use additional hydrogen peroxide which corresponds to the quantity of oxidizing agent required for oxidation into phospholene oxide.

Hydrogen peroxide is preferably used in the form of an aqueous stabilized solution, although it is also possible to use anhydrous solutions. There is no need to use hydrogen peroxide as such. Instead, the reaction may also be carried out with compounds of the type which give off or liberate hydrogen peroxide in the course of the reaction, for example perborates, silicate peroxyhydrates, phosphate peroxyhydrates and hydrogen peroxide-amine adducts.

Suitable catalysts are any osmium compounds which dissolve in the reaction medium, preferably aqueous hydrogen peroxide, and which can be converted by hydrogen peroxide into osmium tetroxide. In addition to osmium tetroxide itself, examples of suitable osmium compounds are the alkali metal osmates, such as potassium osmate for example.

The process according to the invention is generally carried out by adding the solution containing or liberating hydrogen peroxide to a mixture of the osmium catalyst and the phospholene oxide corresponding to formula (II). However, both the osmium catalyst and also the phospholene oxide of formula (II) may be initially introduced on their own and the missing constituent added at the same time as the solution containing or liberating hydrogen peroxide. The end products may also be obtained by mixing all the components and heating the resulting mixture to the reaction temperature. Unfortunately, this procedure involves heat dissipation problems.

In order to obtain complete conversion of the phospholene oxide of formula (II) into a dihydroxy phospholane oxide, about 1.0 to 2.0 moles and preferably about 1.0 to 1.1 moles of hydrogen peroxide are generally used per mole of phospholene oxide. Although larger excesses of hydrogen peroxide are of course possible, they do not provide any economic advantage. If less than 1 mole of hydrogen peroxide is used per mole of phospholene oxide, conversion into dihydroxy phospholane oxides remains incomplete.

The quantity in which the osmium catalyst is used amounts to between about 0.001 and 1.0% by weight of osmium and preferably to between about 0.005 and 0.1% by weight of osmium, based on the quantity of phospholane oxide to be converted. Larger quantities of osmium do not provide any significant advantage.

The reaction temperatures are in the range of about 20° to 150° C and preferably in the range of about 35° to 100° C. Above this temperature range, thermal decomposition becomes a problem, whereas below it the osmium-catalyzed decomposition of the hydrogen peroxide predominates. In general, the reaction is carried out under normal pressure, although superatmospheric or subatmospheric pressures are not harmful. The atmosphere over the reaction mixture is also of minor significance although reducing gases should not be present in it.

The end products of the reaction, the 3,4-dihydroxy phospholane oxides, are generally isolated in pure form by evaporating the solvent. In general, it is advisable to use water as the solvent, although it is also possible for the reaction to be carried out in trialkyl phosphates, for example trimethyl phosphate, in phosphonates, in alcohols, carboxylic acids or esters as solvents.

When the solvent is evaporated off, the catalyst is normally distilled off at the same time in the form of readily volatile osmium tetroxide and excess hydrogen peroxide is decomposed into water and oxygen. Accordingly, the solvent, catalyst and excess oxidation reagent may all be removed at the same time in a single process step.

The invention is illustrated by the following Examples.

EXAMPLE 1

116 g of 1-methyl-1-oxo-3-phospholene and 8 mg of potassium osmate are introduced into 300 ml of water, followed by heating to 50° C. 108 g of a 35% hydrogen peroxide solution are then added dropwise to the stirred reaction mixture over a period of 30 minutes. The temperature of the reaction mixture is kept below 80° C by external cooling. Water is then distilled off at a pressure decreasing to 1 mmHg, the internal temperature remaining below 80° C. The residue left is stirred with 250 ml of methylene chloride. Residues of water are distilled off from this mixture together with the methylene chloride. Evacuation leaves 150 g of 1-methyl-1-oxo-3,4-dihydroxy phospholane in the form of a pale yellow colored powder.

EXAMPLE 2 (Comparison Example)

23 mg of potassium osmate are introduced into a mixture of 116 g of 1-methyl-1-oxo-3-phospholene, 270 ml of water and 108 g of 35% hydrogen peroxide solution which has been cooled from room temperature to 0° C. Despite external cooling, an exothermic reaction brings the temperature of the reaction mixture to 18° C, accompanied by a vigorous evolution of gas. This is followed by stirring for 1 hour at 10° C.

The mixture is then extracted 5 times with 500 ml of chloroform. Concentration by evaporation of the combined chloroform phases leaves behind 102 g of 1-methyl-1-oxo-3-phospholene.

This Example shows that the reaction temperature is a critical parameter.

EXAMPLE 3

A mixture of 116 g of 1-methyl-1-oxo-3-phospholene, 20 mg of potassium osmate and 150 ml of water is heated under reflux to boiling (temperature of the liquid 103° C). 125 g of a 30% hydrogen peroxide solution are added dropwise to the hot reaction solution over a period of 2 hours, the reaction temperature being kept at 103° C by gentle external cooling. After the hydrogen peroxide has been added, the reaction mixture is kept at 105° C for another hour.

Evaporation of the water in vacuo, for which purpose the pressure is lowered to 1 mm Hg and the temperature increased to 140° C, leaves behind 147 g of 1-methyl-1-oxo-3,4-dihydroxy phospholane in the form of a reddish highly viscous oil. The $^1$H-NMR-spectrum shows the presence of P—CH$_3$-protons, C—H-protons and OH-protons in the expected ratio of 3:6:2. No double bonds can be detected.

Carbon, hydrogen and phosphorus analyses confirm the composition indicated.

| Calculated (MW 150) | 40.0% C | 7.34% H | 20.6% P |
| --- | --- | --- | --- |
| Observed | 41.1 | 7.5 | 20.2 |

If, therefore, the reaction temperature is above the preferred temperature range, products containing crystallization-inhibiting impurities are obtained, i.e. the product is an oil rather than a crystalline solid.

EXAMPLE 4

116 g of 1-methyl-1-oxo-3-phospholene (1.0 mole), 270 ml of water and 78 mg of potassium osmate are mixed and the resulting mixture is heated to 70° C. 49 g of a 35% hydrogen peroxide solution (0.505 mole) are then added dropwise over a period of 10 minutes. The highly exothermic reaction is stabilized by external cooling. The reaction temperature is then maintained for 3 hours, followed by concentration by evaporation in vacuo at a maximum sump temperature of 80° C. According to the $^1$H-NMR-spectrum, the liquid yellow residue consists, as expected, of a 1:1-mixture of 1-methyl-1-oxo-3-phospholene and 1-methyl-1-oxo-3,4-dihydroxy phospholane. After a few days, the 1-methyl-1-oxo-3,4-dihydroxy phospholane begins to crystallize out. The two components are separated by the addition of 100 ml of methylene chloride. 1-Methyl-1-oxo-3,4-dihydroxy phospholane (74 g) is left behind in the form of a yellow crystal sludge. 1-Methyl-1-oxo-phospholene (56 g) is obtained in pure form after concentration of the methylene chloride phase and vacuum distillation.

Accordingly, even when hydrogen peroxide is used in a substoichiometric quantity, pure 3,4-dihydroxy phospholane oxides can be obtained as the reaction products.

EXAMPLE 5

66 g of 1-methyl-1-thio-3-phospholene, 8 mg of potassium osmate and 150 ml of water are mixed. 110 g of a 35% hydrogen peroxide solution are slowly added dropwise to the heterogeneous mixture at a temperature of 70° C. The exothermic reaction is accompanied by the deposition of sulfur. After approximately 1 hour, the sulfur precipitated is isolated by filtration and the aqueous filtrate is concentrated by evaporation at a pressure decreasing to 1 mm Hg and at a maximum internal temperature of 80° C. In order to remove residues of water, 100 ml of methylene chloride are added and distilled off again after intensive mixing with the residue. The residue of 1-methyl-1-oxo-3,4-dihydroxy phospholane weighs 69 g.

EXAMPLE 6

130 g of 1-oxo-1,3-dimethyl-3-phospholene, 300 ml of water and 18 mg of potassium osmate are heated together to 40° C. The addition of a hydrogen peroxide solution initiates an exothermic reaction which increases the temperature of the reaction mixture to 70° C. At this temperature, the rest of the 35% hydrogen peroxide solution, amounting in all to 108 g, is added over a period of 20 minutes. The water is then distilled off at 70° C under a pressure decreasing to 1 mm Hg. The residue of 159 g of 1-oxo-1,3-dimethyl-3,4-dihydroxy phospholane is a pale yellow colored viscous oil.

EXAMPLE 7

A total of 105 g of a 35% hydrogen peroxide solution is added dropwise at 60° C to 132 g of 1-methoxy-1-oxo-3-phospholine, 15 mg of potassium osmate and 50 ml of water. The reaction temperature is kept by external cooling at 50°–60° C. The water is then distilled off in vacuo at a temperature of 60° C. The residue comprises 161 g of 1-methoxy-1-oxo-3,4-dihydroxy phospholane, a pale yellow colored viscous liquid.

EXAMPLE 8

116 g of an approximately 1:1 mixture of 1-methyl-1-oxo-2-phospholene and 1-methyl-1-oxo-3-phospholene are mixed with 31 g of potassium osmate and 150 ml of water, the resulting mixture is heated to 70°–80° C and reacted at that temperature with 109 g of a 35% hydrogen peroxide solution. After 3 hours, water is distilled off. The yellow liquid residue is mixed intensively with 3 × 100 ml of CH$_2$Cl$_2$ and washed in this way. Thereafter, the undissolved residue weighs 60 g. The $^1$H-NRM-spectrum agrees with that of 1-methyl-1-oxo-3,4-dihydroxy phospholane. 47 g of 1-methyl-1-oxo-2-phospholene are obtained from the combined methylene chloride phases by concentration through evaporation and vacuum distillation.

EXAMPLE 9

174 g of 1-isobutoxy-1-oxo-3-phospholene, 500 ml of water and 10 g of an approximately 7% solution of osmium tetroxide in water are mixed and 130 g of a 30% hydrogen peroxide solution dissolved in 500 ml of water are added dropwise to the resulting mixture. The temperature is kept between 30° and 40° C by external cooling. Towards the end of the addition, the water is distilled off in vacuo at a maximum temperature of 50° C. The residue comprises 210 g of 1-isobutoxy-1-oxo-3,4-dihydroxy phospholane in the form of a slowly crystallizing viscous liquid.

EXAMPLE 10

194 g of 1-(2-chloropropoxy)-1-oxo-3-phospholene, 500 ml of water and 108 g mg of potassium osmate are heated to 45° C and reacted at 45°–60° C with 124 g of a 40% hydrogen peroxide solution. The hydrogen peroxide solution is added over a period of 20 minutes. Evaporation of the water at a maximum temperature of 60° C in the solution to be concentrated by evaporation leaves behind 229 g of 1-(2-chloropropoxy)-1-oxo-3,4-dihydroxy phospholane.

EXAMPLE 11

148 g of 1-butyl-1-oxo-3-phospholene, 10 mg of potassium osmate and 300 ml of water are heated to 50° C. 108 g of a 35% hydrogen peroxide solution are added dropwise over a period of 30 minutes, the temperature being kept below 60° C. The water is then evaporated off in vacuo at a maximum temperature in the solution of 80° C. The residue of 180 g of 1-butyl-1-oxo-3,4-dihydroxy phospholane is a highly viscous liquid.

EXAMPLE 12

27 g of 1-n-dodecyl-1-oxo-3-phospholene, 50 ml of water and 70 mg of osmium tetroxide in the form of an aqueous solution are mixed and the resulting mixture is heated to 50° C. The gradual addition of 13.5 g of a 30% aqueous hydrogen peroxide solution produces very heavy foaming. On completion of the reaction, the reaction mixture is extracted twice with 500 ml of methylene chloride. After the methylene chloride phases have been carefully concentrated by evaporation, 30 g of 1-n-dodecyl-1-oxo-3,4-dihydroxy phospholane are obtained as a residue.

It will be appreciated that the instant specification and examples are set forth by way of illustration and not limitation, and that various modifications and changes may be made without departing from the spirit and scope of the present invention.

What is claimed is:

1. A process for the preparation of a 3,4-dihydroxy phospholane oxide of the formula

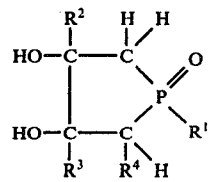

in which
R$^1$ represents an alkyl, alkoxy, alkenyl, alkenyloxy, alkinyl or alkinyloxy with up to 18 carbon atoms and substitution products thereof; aryl and aryloxy having up to 14 carbon atoms and substitution products thereof; cycloalkyl and cycloalkoxy having up to 6 ring carbon atoms and substitution products thereof; dialkylamino having up to 6 carbon atoms per alkyl radical and substitution products thereof; and N-hetero-radicals, and
R$^2$, R$^3$ and R$^4$ independently of one another represent a C$_1$–C$_4$-alkyl radical or hydrogen,
comprising reacting a phospholene oxide of the formula

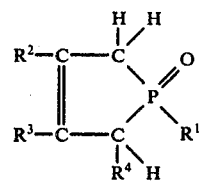

with hydrogen peroxide in the presence of a catalytic amount of an osmium compound at a temperature in the range of about 20° to 150° C.

2. A process as claimed in claim 1, wherein the reaction is carried out at a temperature in the range of about 35° to 100° C.

* * * * *